United States Patent [19]
Collen

[11] Patent Number: 6,001,081
[45] Date of Patent: Dec. 14, 1999

[54] KINK INHIBITING DEVICE

[75] Inventor: Justin Collen, Cape Town, South Africa

[73] Assignee: Dionex Corp., Sunnyvale, Calif.

[21] Appl. No.: 09/145,152

[22] Filed: Sep. 1, 1998

[30] Foreign Application Priority Data

Sep. 2, 1997 [ZA] South Africa .......................... 97/7871

[51] Int. Cl.$^6$ ................................................ A61M 5/32
[52] U.S. Cl. ........................................ 604/174; 604/180
[58] Field of Search .................................. 604/174, 177, 604/179, 180, 523; 128/DIG. 26

[56] References Cited

U.S. PATENT DOCUMENTS

| | | | |
|---|---|---|---|
| 4,711,636 | 12/1987 | Bierman | 604/180 |
| 5,147,320 | 9/1992 | Reynolds et al. | 604/174 |
| 5,626,565 | 5/1997 | Landis et al. | 604/174 |
| 5,690,616 | 11/1997 | Mogg | 604/174 |
| 5,709,665 | 1/1998 | Vergano et al. | 604/174 |

FOREIGN PATENT DOCUMENTS

| | | |
|---|---|---|
| 0 661 187 A1 | 5/1995 | European Pat. Off. . |
| 1567051 | 8/1990 | United Kingdom . |

*Primary Examiner*—John D. Yasko
*Attorney, Agent, or Firm*—Flehr, Hohbach, Test, Albritton & Herbert; David J. Brezner

[57] ABSTRACT

A kink inhibiting device is provided for inhibiting kinking in a length of curved flexible tubing, and in particular IV or drip tubing. The device comprises a pair of U-shaped shell halves which are joined back-to-back at their bight portions by an integral hinge formation. The shell halves each define channels having semi-circular cross-sectional profiles, and are formed with connecting lands carrying studs and complemental apertures for allowing the shell halves to mate with one another. The shell halves each have a radius of curvature (R) which is greater than the maximum radius of curvature at which the flexible tubing starts to kink when unsupported.

11 Claims, 2 Drawing Sheets

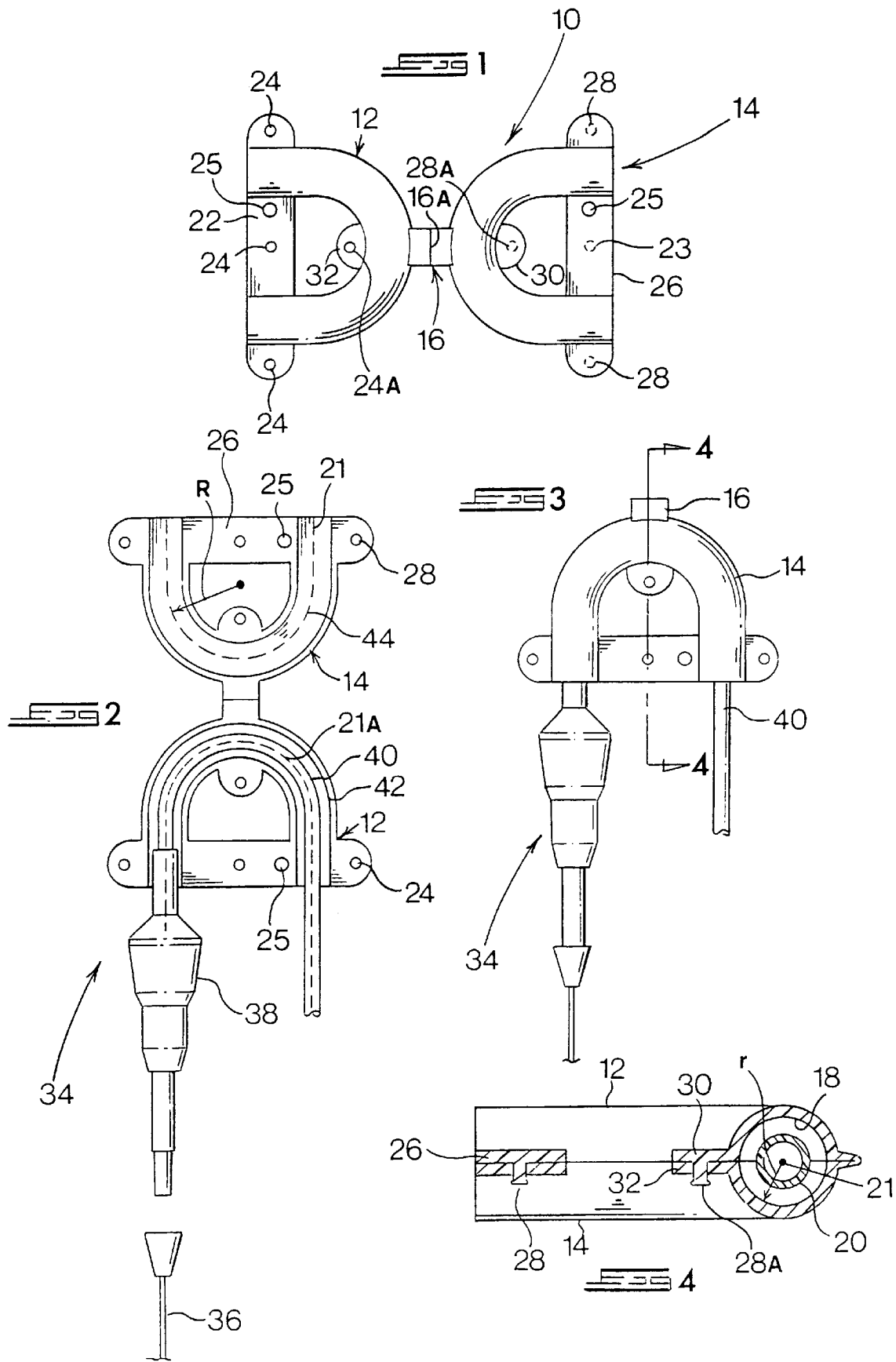

KINK INHIBITING DEVICE

BACKGROUND TO THE INVENTION

This invention relates to a kink inhibiting device for inhibiting kinking in a length of curved flexible tubing.

Intravenous (IV) or drip arrangements generally comprise a raised drip bag connected by a length of IV or drip tubing to a drip cannula or needle. A U-bend is typically formed in that portion of the tubing proximate the needle for allowing the tubing to be fed back to the drip bag. Kinking tends to occur in this U-bend. This causes a reduced flow of fluid into the vein which has been targeted by the cannula. This often leads to clotting in the vein, resulting in the painful and discomforting step of having to relocate the cannula. In addition, once kinking has occurred, the entire drip arrangement needs to be replaced, which is a relatively time-consuming and expensive procedure.

It is an object of the invention to provide a device which inhibits or at least reduces kinking in a drip or IV tube, and which can be fitted to the drip tube when the drip is in situ.

SUMMARY OF THE INVENTION

According to the invention there is provided a kink inhibiting device for inhibiting kinking in a length of curved flexible tubing, the device comprising a conduit which is dimensioned to accommodate the length of tubing, the conduit including two channel-defining shell halves and connecting means for connecting the shell halves together over the length of curved flexible tubing, the shell halves each having a radius of curvature which is greater than the maximum radius of curvature at which the flexible tubing starts to kink when unsupported.

Preferably, the shell halves are hinged to one another, and are substantially U-shaped in plan view, with each shell half defining a channel having a semi-circular profile.

Conveniently, the connection means comprise a first connecting land or flange carried on one shell half, a second connecting land or flange carried on the other shell half so as to provide a connecting interface, and mating formations carried on the lands for holding the lands together in a click or snap fit.

Typically, the mating formations comprise studs and corresponding apertures within which the studs are arranged to locate in a snap or friction fit.

Advantageously, the kink inhibiting device is unitary with an integral hinge and is injection moulded from a hard plastics material such as polypropylene or polyethylene.

Typically, the shell halves are joined back-to-back at their bight portions.

Alternatively, the shell halves may be separate from one another.

Preferably, the ratio of the average radius of curvature R of the central axes of the shell halves to the inner cross sectional radius of curvature r of the channels is greater than 3:1, and is more preferably greater than 3.5:1.

BRIEF DESCRIPTION OF THE DRAWINGS

FIG. 1 shows a top plan view of a kink inhibiting device of the invention in the open position;

FIG. 2 shows an underplan view of the kink inhibiting device of FIG. 1 in the open position in the process of being fitted to a drip tube;

FIG. 3 shows the kink inhibiting device of FIG. 2 closed around the drip tube;

FIG. 4 shows a cross-section on the line 4—4 of FIG. 3; and

DESCRIPTION OF EMBODIMENTS

Figure 5:
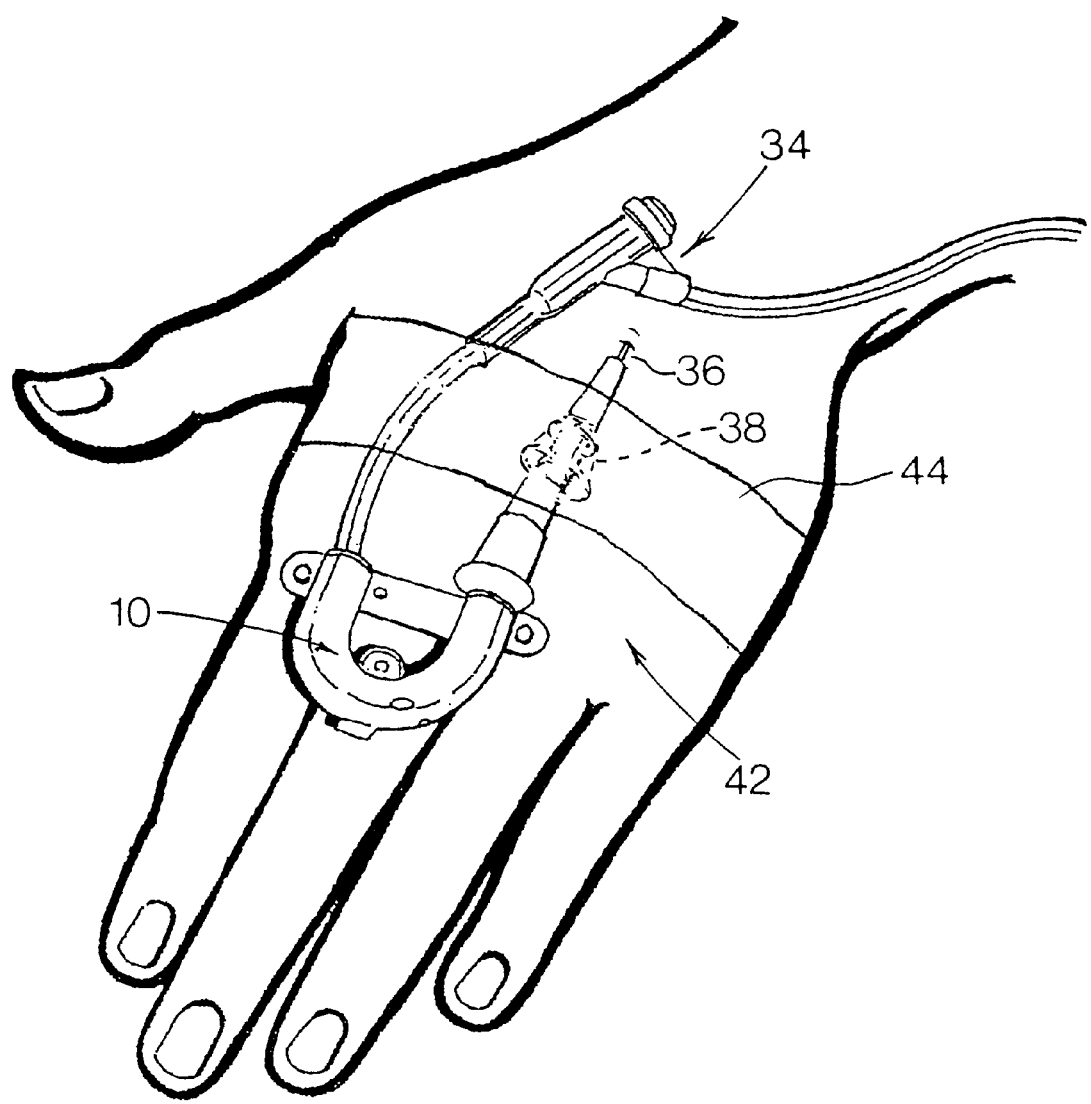
FIG. 5 shows a pictorial view of the kink inhibiting device of FIG. 1 applied when the drip is fitted to a patient.

Referring first to FIG. 1, a unitary kink inhibiting device 10 is injection moulded from a relatively hard and rigid plastics material such as polypropylene or polyethylene, and comprises first and second U-shaped shell halves 12 and 14 which are joined back-to-back by an integral hinge 16 having a line of weakness 16A. As is clear from FIG. 4, the shell halves 12 and 14 have a semi-circular profile 18 which is dimensioned to comfortably accommodate a drip tube 20. The shell halves 12 and 14 each define U-shaped central axes 21 and 21A. The first shell half 12 is formed with a first connecting land 22 extending across the opening of the U and having three apertures 24. An additional pair of registering through-apertures 25 are provided for allowing the device to be anchored to a patient by being stitched to a bandage or the like. The second shell half 14 is provided with a corresponding connecting land 26 formed with three complemental connecting pins or studs 28 which are arranged to extend through the corresponding apertures 24 in a snug friction or click fit when the two shell halves are folded together into the FIG. 4 position. An additional connecting pin 28A is supported on a tag 30 which extends from a bight of the U-shaped channel half 14, and a complemental aperture 24A is formed in a corresponding tag 32 extending from the bight of the U-shaped shell half 12.

In FIG. 2, part of a drip arrangement or intravenous giving set 34 is shown comprising a drip cannula or needle 36 which is fitted into a rubber connecting spigot 38. The spigot is in turn mounted to the end of a curved length of drip tubing 40, which leads to an elevated drip bag (not shown). As was mentioned previously, kinking is most prone to occur in the length of curved tubing 40 proximate the spigot 38. The curved length of tubing is consequently fitted into the first shell half 12, after which the second shell half 14 is folded over into the FIG. 3 position, with the pins 28 in the second shell half extending through the apertures 24 in the first shell half so as to hold the kink inhibiting device in position over the tubing.

The U-shaped shell halves typically have an inner radius of curvature of 9.5 mm and an outer radius of curvature of 16.5 mm, with an average radius of curvature R at the central axes 21 and 21A of 13 mm. The channels 42 and 44 typically have inner cross-sectional radii of curvature r of 3.5 mm, with the ratio of R:r being 13:3.5 or 3.7:1. This ratio is preferably above 3 in order to ensure that the drip tube 40 cannot kink when housed within the kink inhibiting device. The outer radius of the drip tube typically ranges from 1.5 to 1.7 mm, with the result that the channels 42 and 44 provide more than sufficient clearance to accommodate this tubing, as well as tubing having a radius of up to 3.3 mm or even 3.4 mm. Naturally, the channel dimensions as well as the radius of curvature of the shell halves may be increased to accommodate even thicker tubing. It should be appreciated that the propensity of the tubing to kink depends on a number of factors, including the material from which the tubing is made, the wall thickness of the tubing, and the temperature of the tubing. At room temperatures of 18° C. to 20° C., the tubing is relatively firm and kink-resistant. At higher temperatures of 37° C. or more, corresponding to the body temperature of the patient against whom the tubing is resting, the tubing tends to soften and to kink more easily.

The kink-inhibiting device has an R:r ratio of 3 or more, which makes allowances for such differences in temperature, material, and wall thickness.

Referring now to FIG. 5, the drip arrangement or intravenous giving set 34 is shown in situ on a hand 42 of a patient, with the kink inhibiting device 10 in position. The drip cannula or needle 36 is located in a wrist vein of the patient, and the connecting spigot 38 and drip tube 40 is anchored in position using a length of sticking plaster 44.

A major advantage of the kink inhibiting device of the invention is that, in contrast to kink-inhibiting sleeves and the like, it can conveniently be retrofitted to a drip which is already in position on a patient without the need to remove any portion of the drip tube or to manoeuvre the drip tube unnecessarily.

The invention is not confined to preventing or reducing kinking in a drip tube, but may be used to prevent kinking in any flexible tube or hose which is designed to carry a fluid and which normally undergoes bending.

I claim:

1. A kink inhibiting device for inhibiting kinking in a length of curved flexible tubing, the device comprising a conduit which is dimensioned to accommodate the length of tubing, the conduit including two channel-defining shell halves and connecting means for connecting the shell halves together over the length of curved flexible tubing, the shell halves each having a radius of curvature which is greater than the maximum radius of curvature at which the flexible tubing starts to kink when unsupported.

2. A kink inhibiting device according to claim 1 in which the shell halves are substantially U-shaped in plan view.

3. A kink inhibiting device according to claim 1 in which each shell half defines a channel which has a semi-circular cross-sectional profile.

4. A kink inhibiting device according to claim 1 in which the shell halves are hinged to one another.

5. A kink inhibiting device according to claim 4 in which the shell halves are provided with an integral hinge formation, with the entire device being unitary and being injection moulded from a plastics material.

6. A kink inhibiting device according to claim 5 in which the shell halves are joined back-to-back at their bight portions by the integral hinge formation.

7. A kink inhibiting device according to claim 1 in which the shell halves are separate from one another.

8. A kink inhibiting device according to claim 1 in which the connection means comprise a first connecting land or flange carried on one shell half, a second connecting land or flange carried on the other shell half so as to provide a connecting interface, and mating formations carried on the lands for holding the lands together in a click or snap fit.

9. A kink inhibiting device according to claim 8 in which the mating formations comprise studs and corresponding apertures within which the studs are arranged to locate in a snap or friction fit.

10. A kink inhibiting device according to claim 1 in which the length of flexible tubing is drip or IV tubing, with the device being arranged to be fitted to that portion of tubing proximate a spigot to which a drip cannula or needle is adapted to be connected.

11. A kink inhibiting device according to claim 1 in which the ratio of the average radius of curvature R of central axes of the channels of the shell halves to the inner cross sectional radius of curvature r of the channels is greater than 3:1.

* * * * *

UNITED STATES PATENT AND TRADEMARK OFFICE
CERTIFICATE OF CORRECTION

PATENT NO. : 6,001,081
DATED : December 14, 1999
INVENTOR(S) : Collen

It is certified that error appears in the above-identified patent and that said Letters Patent is hereby corrected as shown below:

[73] Assignee,

Column 1,
Delete all of section [73], including the name of the assignee, "Dionex Corp., Sunnyvale, Calif."

Signed and Sealed this

Twenty-fifth Day of September, 2001

*Attest:*

*Attesting Officer*

NICHOLAS P. GODICI
*Acting Director of the United States Patent and Trademark Office*